(12) United States Patent
Christensen et al.

(10) Patent No.: US 7,802,824 B2
(45) Date of Patent: Sep. 28, 2010

(54) CONNECTING PIECE FOR A TUBING

(75) Inventors: Bjarne Lasse Christensen, Køge (DK); Trygve Kalf Hansen, Fuglebjerg (DK)

(73) Assignee: Unomedical A/S, Birkeroed (DK)

( * ) Notice: Subject to any disclaimer, the term of this patent is extended or adjusted under 35 U.S.C. 154(b) by 643 days.

(21) Appl. No.: 10/536,535

(22) PCT Filed: Nov. 26, 2003

(86) PCT No.: PCT/DK03/00809

§ 371 (c)(1),
(2), (4) Date: Feb. 28, 2006

(87) PCT Pub. No.: WO2004/047909

PCT Pub. Date: Jun. 10, 2004

(65) Prior Publication Data

US 2006/0157981 A1  Jul. 20, 2006

(30) Foreign Application Priority Data

Nov. 26, 2002  (DK) ............................... 2002 01823

(51) Int. Cl.
*F16L 21/00* (2006.01)
(52) U.S. Cl. ............... 285/399; 285/307; 285/330; 285/921; 285/913
(58) Field of Classification Search ............ 285/399, 285/331, 921, 913, 307, 330
See application file for complete search history.

(56) References Cited

U.S. PATENT DOCUMENTS

| | | | |
|---|---|---|---|
| 643,544 A | | 2/1900 | Simmons |
| 1,260,690 A | * | 3/1918 | Liady .................. 285/330 |
| 1,838,825 A | | 1/1929 | Goldstein |
| 1,759,337 A | * | 5/1930 | Zublin .................. 464/21 |
| 1,991,103 A | | 2/1935 | King |
| 2,047,010 A | | 7/1936 | Dickinson |
| 2,195,492 A | * | 4/1940 | McDonald .................. 285/913 |
| 2,295,849 A | | 9/1942 | Kayden |
| 2,307,275 A | * | 1/1943 | Johnson .................. 285/36 |
| 2,314,867 A | * | 3/1943 | Boynton .................. 285/81 |
| 2,319,731 A | | 5/1943 | Garrett |
| 2,464,744 A | * | 3/1949 | Fennema .................. 285/330 |
| 2,471,759 A | * | 5/1949 | Lowrey .................. 285/110 |
| 2,473,909 A | * | 6/1949 | Ruchti .................. 285/330 |

(Continued)

FOREIGN PATENT DOCUMENTS

DE    893 296    12/1953

(Continued)

*Primary Examiner*—Aaron M Dunwoody
(74) *Attorney, Agent, or Firm*—Brinks Hofer Gilson & Lione

(57) ABSTRACT

A connecting piece for a tubing including a first unit and a second unit is provided. The first unit includes a first connecting element for a tubing element and a second connecting part for the second unit. The second connecting element includes a tubular female part for engagement with the second unit and first sealing elements, and the second unit includes a tubular male part with a collar and second sealing elements for cooperating with the first sealing elements. The first and second units further include separator elements. The first sealing elements and the second sealing elements are configured for mutual locking engagement by moving a male part and a female part axially towards each other.

21 Claims, 8 Drawing Sheets

U.S. PATENT DOCUMENTS

| | | | |
|---|---|---|---|
| 2,533,731 A | 12/1950 | Gomberg | |
| 2,630,803 A | 3/1953 | Baran | |
| 2,690,529 A | 9/1954 | Lindblad | |
| 2,730,099 A | 1/1956 | Sullivan | |
| 2,819,914 A * | 1/1958 | Eitner | 285/70 |
| 2,839,060 A | 6/1958 | Ormo | |
| 2,936,141 A | 5/1960 | Rapata | |
| 2,952,420 A | 9/1960 | Von Hoorn | |
| 3,055,361 A | 9/1962 | Ballard | |
| 3,074,541 A | 1/1963 | Roehr | |
| 3,107,785 A | 10/1963 | Roehr | |
| 3,136,367 A * | 6/1964 | Wright et al. | 166/208 |
| 3,154,080 A | 10/1964 | Rowan et al. | |
| 3,204,992 A * | 9/1965 | Walker | 285/330 |
| 3,219,373 A * | 11/1965 | Sutliff | 403/34 |
| 3,283,780 A * | 11/1966 | Sutton | 137/614.04 |
| 3,317,166 A | 5/1967 | Janssen | |
| 3,545,286 A | 12/1970 | Stenstrom | |
| 3,610,240 A | 10/1971 | Harautuneian | |
| 3,623,753 A * | 11/1971 | Henry | 285/330 |
| 3,648,999 A | 3/1972 | Bauer | |
| 3,783,996 A | 1/1974 | Gerard et al. | |
| 3,814,097 A | 6/1974 | Ganderton et al. | |
| 3,831,729 A | 8/1974 | Howard | |
| 3,840,011 A | 10/1974 | Wright | |
| 3,865,236 A | 2/1975 | Rycroft | |
| 3,942,528 A | 3/1976 | Loeser | |
| 3,986,508 A | 10/1976 | Barrington | |
| 4,014,328 A | 3/1977 | Cluff et al. | |
| 4,022,205 A | 5/1977 | Tenczar | |
| 4,077,657 A * | 3/1978 | Trzeciak | 285/184 |
| 4,146,113 A | 3/1979 | Gavel | |
| 4,150,798 A | 4/1979 | Aragon | |
| 4,188,950 A | 2/1980 | Wardlaw | |
| 4,201,406 A | 5/1980 | Dennehey et al. | |
| 4,227,528 A | 10/1980 | Wardlaw | |
| 4,267,836 A | 5/1981 | Whitney et al. | |
| 4,306,705 A | 12/1981 | Svensson | |
| 4,315,505 A | 2/1982 | Crandall et al. | |
| 4,328,839 A * | 5/1982 | Lyons et al. | 138/120 |
| 4,334,551 A | 6/1982 | Pfister | |
| D267,199 S | 12/1982 | Koenig | |
| 4,365,630 A | 12/1982 | McFlarlane | |
| 4,400,861 A | 8/1983 | Parker | |
| 4,406,042 A | 9/1983 | McPhee | |
| 4,458,344 A | 7/1984 | Coogler | |
| 4,472,024 A | 9/1984 | Konomura et al. | |
| 4,473,369 A | 9/1984 | Lueders et al. | |
| 4,487,433 A * | 12/1984 | Miller | 285/81 |
| 4,500,312 A | 2/1985 | McFarlane | |
| 4,517,971 A | 5/1985 | Sorbonned | |
| 4,530,695 A | 7/1985 | Phillips et al. | |
| 4,531,686 A | 7/1985 | Shaw | |
| 4,576,846 A | 3/1986 | Noel | |
| 4,606,735 A | 8/1986 | Wilder et al. | |
| 4,610,469 A | 9/1986 | Wolff-Mooij | |
| 4,616,790 A | 10/1986 | Beltran | |
| 4,619,349 A | 10/1986 | Braun | |
| 4,635,683 A | 1/1987 | Nielsen | |
| 4,637,404 A | 1/1987 | Gessman | |
| 4,662,873 A | 5/1987 | Lash et al. | |
| 4,682,702 A | 7/1987 | Gach | |
| 4,713,059 A | 12/1987 | Bickelhaupt et al. | |
| 4,734,092 A | 3/1988 | Millerd | |
| 4,755,173 A | 7/1988 | Konopka et al. | |
| 4,758,020 A | 7/1988 | Boyd | |
| 4,800,629 A | 1/1989 | Ikeda | |
| 4,802,638 A | 2/1989 | Burger et al. | |
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,878,897 A | 11/1989 | Katzin | |
| 4,895,570 A | 1/1990 | Larkin | |
| D306,500 S | 3/1990 | Brahler | |
| 4,913,369 A | 4/1990 | Lia et al. | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,978,338 A | 12/1990 | Melsky et al. | |
| 4,982,842 A | 1/1991 | Hollister | |
| 4,986,817 A | 1/1991 | Code | |
| 4,994,045 A | 2/1991 | Ranford | |
| 5,011,475 A | 4/1991 | Olsen | |
| 5,024,662 A | 6/1991 | Menes et al. | |
| 5,067,496 A | 11/1991 | Eisele | |
| 5,077,872 A | 1/1992 | Guthammar | |
| 5,083,757 A | 1/1992 | Barsky | |
| 5,098,389 A | 3/1992 | Cappucci | |
| 5,112,313 A | 5/1992 | Sallee | |
| 5,116,319 A | 5/1992 | Van den Haak | |
| 5,116,324 A | 5/1992 | Brierley et al. | |
| 5,116,325 A | 5/1992 | Paterson | |
| 5,121,751 A | 6/1992 | Panalletta | |
| 5,134,593 A | 7/1992 | Logan et al. | |
| 5,134,594 A | 7/1992 | Woo | |
| 5,137,524 A | 8/1992 | Lynn et al. | |
| 5,141,496 A | 8/1992 | Dalto et al. | |
| 5,147,319 A | 9/1992 | Ishikawa et al. | |
| 5,147,375 A | 9/1992 | Sullivan et al. | |
| 5,161,681 A | 11/1992 | Kemp et al. | |
| 5,163,915 A | 11/1992 | Holleron | |
| 5,176,662 A | 1/1993 | Bartholomew et al. | |
| 5,188,314 A | 2/1993 | Peters | |
| 5,188,611 A | 2/1993 | Orgain | |
| RE34,223 E | 4/1993 | Bonaldo | |
| 5,222,947 A | 6/1993 | D'Amico | |
| 5,232,454 A | 8/1993 | Hollister | |
| 5,236,143 A | 8/1993 | Dragon | |
| 5,240,199 A | 8/1993 | Peters | |
| 5,248,301 A | 9/1993 | Koenig et al. | |
| 5,256,152 A | 10/1993 | Marks | |
| 5,257,980 A | 11/1993 | Van Antwerp et al. | |
| 5,265,822 A | 11/1993 | Shober, Jr. et al. | |
| 5,269,799 A | 12/1993 | Daniel | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,343,637 A | 9/1994 | Schindler | |
| 5,350,392 A | 9/1994 | Purcell et al. | |
| 5,354,280 A | 10/1994 | Haber et al. | |
| 5,366,469 A | 11/1994 | Steg et al. | |
| 5,372,592 A | 12/1994 | Gambale | |
| 5,376,082 A | 12/1994 | Phelps | |
| 5,380,067 A | 1/1995 | Turvill et al. | |
| 5,384,174 A | 1/1995 | Ward et al. | |
| 5,387,197 A | 2/1995 | Smith et al. | |
| 5,388,931 A | 2/1995 | Carlson | |
| 5,390,669 A | 2/1995 | Stuart et al. | |
| 5,391,151 A | 2/1995 | Wilmot | |
| 5,403,288 A | 4/1995 | Stanners | |
| 5,405,332 A | 4/1995 | Opalek | |
| 5,429,607 A | 7/1995 | McPhee | |
| 5,429,613 A | 7/1995 | D'Amico | |
| 5,433,307 A | 7/1995 | Jeppe | |

| | | | | | | |
|---|---|---|---|---|---|---|
| D362,718 S | 9/1995 | Deily et al. | | 6,086,008 A | 7/2000 | Gray et al. |
| 5,449,349 A | 9/1995 | Sallee et al. | | 6,086,575 A | 7/2000 | Mejslov |
| 5,487,506 A | 1/1996 | Drummond et al. | | 6,090,068 A | 7/2000 | Chanut |
| 5,490,841 A | 2/1996 | Landis | | 6,093,172 A | 7/2000 | Funderburk et al. |
| 5,492,313 A | 2/1996 | Pan et al. | | 6,093,179 A | 7/2000 | O'Hara et al. |
| 5,505,709 A | 4/1996 | Funderburk et al. | | 6,099,503 A | 8/2000 | Stradella |
| 5,507,730 A | 4/1996 | Haber et al. | | 6,105,218 A | 8/2000 | Reekie |
| 5,519,167 A | 5/1996 | Kunimoto et al. | | 6,120,482 A | 9/2000 | Szabo |
| 5,520,654 A | 5/1996 | Wahlberg | | 6,123,690 A | 9/2000 | Mejslov |
| 5,522,803 A | 6/1996 | Teissen-Simony | | 6,132,755 A | 10/2000 | Eicher et al. |
| 5,533,974 A | 7/1996 | Gaba | | 6,183,464 B1 | 2/2001 | Sharp et al. |
| 5,540,709 A | 7/1996 | Ramel | | 6,193,694 B1 | 2/2001 | Bell et al. |
| 5,545,143 A | 8/1996 | Fischell | | 6,219,574 B1 | 4/2001 | Cormier et al. |
| 5,545,152 A | 8/1996 | Funderburk et al. | | 6,221,058 B1 | 4/2001 | Kao et al. |
| 5,554,130 A | 9/1996 | McDonald et al. | | 6,248,093 B1 | 6/2001 | Moberg |
| 5,558,650 A | 9/1996 | McPhee | | 6,279,962 B1 * | 8/2001 | McGarian et al. ............. 285/12 |
| 5,562,636 A | 10/1996 | Utterberg | | 6,293,925 B1 | 9/2001 | Safabash et al. |
| 5,584,813 A | 12/1996 | Livingston et al. | | 6,302,866 B1 | 10/2001 | Marggi |
| 5,586,791 A * | 12/1996 | Kirchner et al. ............. 285/179 | | 6,319,232 B1 | 11/2001 | Kashmer |
| 5,591,188 A | 1/1997 | Waisman | | 6,322,535 B1 | 11/2001 | Hitchins et al. |
| 5,599,309 A | 2/1997 | Marshall et al. | | 6,322,808 B1 | 11/2001 | Trautman et al. |
| 5,599,315 A | 2/1997 | McPhee | | 6,334,856 B1 | 1/2002 | Allen et al. |
| 5,599,318 A | 2/1997 | Sweeney et al. | | 6,355,021 B1 | 3/2002 | Nielsen et al. |
| 5,628,765 A | 5/1997 | Morita | | 6,379,335 B1 | 4/2002 | Rigon et al. |
| 5,643,214 A | 7/1997 | Marshall | | D456,692 S | 5/2002 | Epstein |
| 5,643,216 A | 7/1997 | White | | 6,387,076 B1 | 5/2002 | Van Landuyt |
| 5,643,220 A | 7/1997 | Cosme | | 6,460,900 B1 * | 10/2002 | Bakke ........................ 285/330 |
| 5,662,617 A | 9/1997 | Odell et al. | | 6,488,663 B1 | 12/2002 | Steg |
| 5,665,071 A | 9/1997 | Wyrick | | 6,517,517 B1 | 2/2003 | Farrugia et al. |
| 5,665,075 A | 9/1997 | Gyure et al. | | 6,520,938 B1 | 2/2003 | Funderburk et al. |
| 5,681,323 A | 10/1997 | Arick | | D472,316 S | 3/2003 | Douglas et al. |
| 5,695,476 A | 12/1997 | Harris | | D472,630 S | 4/2003 | Douglas et al. |
| 5,704,920 A | 1/1998 | Gyure | | 6,572,586 B1 | 6/2003 | Wojcik |
| 5,709,516 A | 1/1998 | Peterson et al. | | 6,579,267 B2 | 6/2003 | Lynch et al. |
| 5,714,225 A | 2/1998 | Hansen et al. | | 6,582,397 B2 | 6/2003 | Alesi et al. |
| 5,741,288 A | 4/1998 | Rife | | 6,595,962 B1 | 7/2003 | Perthu |
| 5,752,923 A | 5/1998 | Terwilliger | | 6,607,509 B2 | 8/2003 | Bobroff et al. |
| 5,785,357 A * | 7/1998 | Foster et al. .................. 285/92 | | 6,607,511 B2 | 8/2003 | Bobroff et al. |
| 5,794,985 A * | 8/1998 | Mallis ......................... 285/93 | | 6,629,949 B1 | 10/2003 | Douglas |
| 5,810,835 A | 9/1998 | Ryan et al. | | 6,645,182 B1 | 11/2003 | Szabo |
| 5,820,598 A | 10/1998 | Gazza et al. | | 6,685,674 B2 | 2/2004 | Douglas et al. |
| D402,538 S | 12/1998 | Wagter et al. | | 6,702,779 B2 | 3/2004 | Connelly et al. |
| 5,843,001 A | 12/1998 | Goldenberg | | 6,726,649 B2 | 4/2004 | Swenson et al. |
| 5,851,197 A | 12/1998 | Marano et al. | | 6,736,797 B1 | 5/2004 | Larsen et al. |
| 5,858,001 A | 1/1999 | Tsals et al. | | 6,749,589 B1 | 6/2004 | Douglas et al. |
| 5,865,806 A | 2/1999 | Howell | | 6,790,199 B1 | 9/2004 | Gianakos |
| 5,873,540 A | 2/1999 | Hardin | | 6,805,686 B1 | 10/2004 | Fathallah et al. |
| 5,899,886 A | 5/1999 | Cosme | | 6,811,545 B2 | 11/2004 | Vaillancourt |
| 5,913,846 A | 6/1999 | Szabo | | 6,814,720 B2 | 11/2004 | Olsen et al. |
| 5,915,640 A | 6/1999 | Wagter et al. | | 6,824,530 B2 | 11/2004 | Wagner et al. |
| 5,919,167 A | 7/1999 | Mulhauser et al. | | 6,824,531 B1 | 11/2004 | Zecha, Jr. et al. |
| 5,925,032 A | 7/1999 | Clements | | 6,830,562 B2 | 12/2004 | Mogensen et al. |
| 5,947,935 A | 9/1999 | Rhinehart et al. | | 6,837,877 B2 | 1/2005 | Zurcher |
| 5,950,744 A * | 9/1999 | Hughes ........................ 175/320 | | 6,840,922 B2 | 1/2005 | Nielsen et al. |
| 5,951,523 A | 9/1999 | Osterlind et al. | | 6,880,701 B2 | 4/2005 | Bergeron et al. |
| 5,954,643 A | 9/1999 | VanAntwerp et al. | | 6,916,017 B2 | 7/2005 | Noe |
| 5,957,892 A | 9/1999 | Thorne | | 6,923,791 B2 | 8/2005 | Douglas |
| 5,968,011 A | 10/1999 | Larsen et al. | | 6,926,694 B2 | 8/2005 | Marano-Ford et al. |
| 5,975,120 A | 11/1999 | Novosel | | 6,939,331 B2 | 9/2005 | Ohshima |
| 5,980,488 A | 11/1999 | Thorne | | 6,949,084 B2 | 9/2005 | Marggi et al. |
| 5,980,506 A | 11/1999 | Mathiasen | | 7,344,165 B2 * | 3/2008 | Le Quere et al. ............. 285/307 |
| 5,984,224 A | 11/1999 | Yang | | 7,390,032 B2 * | 6/2008 | Hughes ...................... 285/330 |
| 5,984,897 A | 11/1999 | Petersen et al. | | 7,448,655 B2 * | 11/2008 | Le Bars ...................... 285/323 |
| 5,992,787 A | 11/1999 | Burke | | 2001/0004970 A1 | 6/2001 | Hollister et al. |
| D417,773 S | 12/1999 | Howell et al. | | 2001/0016714 A1 | 8/2001 | Bell et al. |
| 6,017,328 A | 1/2000 | Fischell et al. | | 2001/0021827 A1 | 9/2001 | Ferguson et al. |
| D421,119 S | 2/2000 | Musgrave et al. | | 2001/0039401 A1 | 11/2001 | Ferguson et al. |
| 6,039,629 A | 3/2000 | Mitchell | | 2001/0041875 A1 | 11/2001 | Higuchi et al. |
| 6,042,570 A | 3/2000 | Bell et al. | | 2002/0022855 A1 | 2/2002 | Bobroff et al. |
| 6,045,533 A | 4/2000 | Kriesel et al. | | 2002/0068904 A1 | 6/2002 | Pluth et al. |
| 6,050,976 A | 4/2000 | Thorne et al. | | 2002/0072720 A1 | 6/2002 | Hague et al. |
| 6,056,718 A | 5/2000 | Funderburk et al. | | 2002/0077599 A1 | 6/2002 | Wojcik |
| 6,074,371 A | 6/2000 | Fischell | | 2002/0107489 A1 | 8/2002 | Lee |

| Publication No. | Date | Inventor |
|---|---|---|
| 2002/0111581 A1 | 8/2002 | Sasso |
| 2002/0145073 A1 | 10/2002 | Swanson et al. |
| 2002/0156424 A1 | 10/2002 | Suzuki et al. |
| 2002/0156427 A1 | 10/2002 | Suzuki et al. |
| 2002/0161332 A1 | 10/2002 | Ramey |
| 2002/0169419 A1 | 11/2002 | Steg |
| 2002/0173748 A1 | 11/2002 | McConnell et al. |
| 2002/0175519 A1* | 11/2002 | Mack et al. ............... 285/330 |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0069548 A1 | 4/2003 | Connelly et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0216686 A1 | 11/2003 | Lynch et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0026840 A1 | 2/2004 | Eckel et al. |
| 2004/0044306 A1 | 3/2004 | Lynch et al. |
| 2004/0049159 A1 | 3/2004 | Barrus et al. |
| 2004/0068231 A1 | 4/2004 | Blondeau |
| 2004/0087913 A1 | 5/2004 | Rogers et al. |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0199123 A1 | 10/2004 | Nielsen |
| 2004/0204687 A1 | 10/2004 | Mogensen et al. |
| 2004/0204690 A1 | 10/2004 | Yashiro et al. |
| 2004/0207202 A1* | 10/2004 | Parks ..................... 285/391 |
| 2004/0220528 A1 | 11/2004 | Garcia, Jr. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0023831 A1* | 2/2005 | Hughes ..................... 285/330 |
| 2005/0035014 A1 | 2/2005 | Cane |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119637 A1 | 6/2005 | Lundgren et al. |
| 2005/0124936 A1 | 6/2005 | Mogensen et al. |
| 2005/0159709 A1 | 7/2005 | Wilkinson |
| 2005/0215979 A1 | 9/2005 | Kornerup et al. |
| 2005/0251098 A1 | 11/2005 | Wyss et al. |
| 2005/0277892 A1 | 12/2005 | Chen |
| 2005/0283114 A1 | 12/2005 | Bresina et al. |
| 2006/0030815 A1 | 2/2006 | Csincsura et al. |

FOREIGN PATENT DOCUMENTS

| | | |
|---|---|---|
| DE | 1 053 541 | 3/1959 |
| DE | DT 26 20 009 A1 | 12/1977 |
| DE | DT 26 200 09 A1 | 12/1977 |
| DE | 28 03 509 | 8/1979 |
| DE | 28 035 09 A | 8/1979 |
| DE | 37 15 965 A | 1/1988 |
| DE | 38 23 447 | 2/1996 |
| DE | 196 31 921 | 3/1997 |
| DE | 196 10 692 A1 | 9/1997 |
| DE | 298 18 311 U1 | 3/1999 |
| DE | 298 18 311 U1 | 11/1999 |
| DE | 198 47 143 A1 | 1/2000 |
| DE | 19847143 A1 | 1/2000 |
| DE | 101 06 074 A1 | 9/2000 |
| DE | 299 21 406 | 1/2001 |
| DE | 100 49 001 A1 | 4/2002 |
| DE | 101 06 074 A1 | 6/2002 |
| DE | 299 21 406 U1 | 11/2002 |
| DK | 37 22 893 C1 | 6/1988 |
| EP | 0 188 014 B1 | 10/1985 |
| EP | 0 239 244 B1 | 2/1987 |
| EP | 0 298 521 B1 | 9/1990 |
| EP | 0 184 231 B1 | 1/1992 |
| EP | 0 475 857 | 3/1992 |
| EP | 0 544 837 B1 | 6/1993 |
| EP | 0 663 039 | 7/1994 |
| EP | 0 651 662 B1 | 5/1995 |
| EP | 0 714 631 B1 | 6/1996 |
| EP | 744 183 A2 | 11/1996 |
| EP | 0 747 006 A1 | 12/1996 |
| EP | 0 688 232 B1 | 12/1998 |
| EP | 0 884 108 A1 | 12/1998 |
| EP | 0 916 361 A1 | 5/1999 |
| EP | 0 931 560 A1 | 7/1999 |
| EP | 0 956 879 A1 | 11/1999 |
| EP | 1 045 145 A1 | 10/2000 |
| EP | 1 060 757 A1 | 12/2000 |
| EP | 1 086 718 A | 3/2001 |
| EP | 1 125 593 A1 | 8/2001 |
| EP | 1 167 765 A2 | 1/2002 |
| EP | 0 775 501 | 6/2002 |
| EP | 0 894 216 B1 | 7/2003 |
| EP | 1 380 315 A1 | 1/2004 |
| EP | 0 956 879 A1 | 7/2004 |
| FR | 576 849 | 8/1924 |
| FR | 576849 | 8/1924 |
| FR | 2 611 013 | 8/1988 |
| FR | 2725902 | 10/1994 |
| FR | 2 733 915 | 11/1996 |
| FR | 2733915 A1 | 11/1996 |
| FR | 2 781 617 A1 | 1/2000 |
| FR | 2781617 A1 | 1/2000 |
| GB | 478803 | 1/1938 |
| GB | 591 730 | 3/1946 |
| GB | 906574 | 9/1962 |
| GB | 1 268 575 | 3/1972 |
| GB | 1 403 034 | 8/1975 |
| GB | 2 224 808 A | 5/1990 |
| GB | 2 270 552 A | 3/1994 |
| JP | 05326062 A | 12/1993 |
| JP | 5326062 A | 12/1993 |
| JP | 7051251 | 11/1995 |
| JP | 9217584 A | 9/1997 |
| JP | 2000-59877 A | 2/2000 |
| JP | 3140740 | 2/2000 |
| JP | 2000059877 A | 2/2000 |

| | | |
|---|---|---|
| JP | 3140740 B2 | 3/2001 |
| JP | 2002-028246 | 1/2002 |
| NL | 1017427 C | 11/2002 |
| WO | WO 87/06474 | 11/1987 |
| WO | WO 93/03787 | 3/1993 |
| WO | WO 93/05840 | 4/1993 |
| WO | WO 94/20160 | 9/1994 |
| WO | WO 95/28327 A | 10/1995 |
| WO | WO 96/35472 A1 | 11/1996 |
| WO | WO 98/09065 | 3/1998 |
| WO | WO 98/58693 | 12/1998 |
| WO | WO 99/07435 | 2/1999 |
| WO | WO 99/33504 | 7/1999 |
| WO | WO 99/36009 | 7/1999 |
| WO | WO 99/56802 | 11/1999 |
| WO | WO 99/61815 | 12/1999 |
| WO | WO 00/02614 | 1/2000 |
| WO | WO 00/03757 | 1/2000 |
| WO | WO 00/44324 A1 | 8/2000 |
| WO | WO 01/04507 A1 | 1/2001 |
| WO | WO 01/30419 A2 | 5/2001 |
| WO | WO 01/68180 | 9/2001 |
| WO | WO 01/81785 A1 | 11/2001 |
| WO | WO 01/93926 A2 | 12/2001 |
| WO | WO 02/46080 | 6/2002 |
| WO | WO 02/066854 A1 | 8/2002 |
| WO | WO 02/068014 | 9/2002 |
| WO | WO 02/094352 | 11/2002 |
| WO | WO 02/100457 | 12/2002 |
| WO | WO 03/015860 A1 | 2/2003 |
| WO | WO 03/026728 | 4/2003 |
| WO | WO 2004/030726 A | 4/2004 |
| WO | WO 2004/087240 | 10/2004 |
| WO | WO 2005/004973 | 1/2005 |

\* cited by examiner

CONNECTING PIECE FOR A TUBING

This application claims the benefit under 35 U.S.C. §371 of International Application No. PCT/DK2003/000809, filed Nov. 26, 2003, which claims priority to Danish Application No. PA 2002 01823, filed Nov. 26, 2002.

The invention relates to a connecting piece for a tubing comprising a first unit and a second unit, said first unit comprising a first connecting element for a tubing element and a second connecting element for the second unit, said second connecting element comprising a tubular female part for engagement with the second unit, and first sealing elements, and said second unit comprising a tubular male part with a collar; and second sealing elements for cooperating with the first sealing elements; said first and second units further comprising separator elements.

DE-U-29818311 teaches a connecting piece in particular for medical infusion systems. That connecting piece comprises a male and a female part, wherein the male part is further provided with a collar with undercuts, said undercuts fitting into a corresponding collar on the female part such that the two undercuts combine to form a kind of hook connection, whereby the male and the female parts are securely locked by means of those devices when the connecting piece is assembled. However, it is associated with the drawback that said locking elements that also serve more or less as separator elements are arranged externally on the connecting piece, with an ensuing increased risk of breaking off or becoming damaged during mounting or dismounting. Likewise, it is a matter of concern that when used repeatedly the hooks will come to suffer from material fatigue and break due to the forces to which they are exposed, in particular during dismounting. The minute these locking elements break off, the connecting piece is very likely to leak, due to the sealing as such being accomplished exclusively by a press-fitting between the inner face of the female part and the outer faces of the male part.

Moreover, the system is associated with the drawback that when the male and the female part are to be separated it is possible to perform this only the one way around, and likewise assembly presupposes orientation of the male and the female part and that the turning takes place in a direction opposite that of the dismounting.

It is thus the object of the present invention to provide a connecting piece, whereby said problems are solved. As opposed to the ones taught in the German utility mode, the present invention provides good locking and sealing of the assembly without a risk of leakage and unintentional separation from each other of the two connecting parts, the lock thus being internal and protected, which ensures good engagement simultaneously with the separator elements operating independently of lock as well as sealing. Moreover these separator elements can further be activated independently of orientation and while providing a relatively small and controlled force. This further contributes to reducing the risk of damaging the connecting pieces both during assembly and separation.

One aspect of the present invention provides a connecting piece having first and second sealing elements. The first and second sealing elements are configured for being mutually engageable by moving the male part and the female part axially towards each other to establish a lock keep the first and second units together. The connecting piece also includes separator elements having a face arranged on the female apart and a face on the male part where the facing are in abutment against each other. The faces are such that turning of the first unit in relation to the second unit, an axially extending positive force component is provided for. The separator elements are arranged at an axial distance from the lock.

By the invention the sealing elements comprise, on the first unit and on the second unit, preferably tooth-like protrusions with faces that extend transversally to the axial extension of the male part and the female part, and that exhibit an inclination in the direction of the periphery of the male/male part in relation to said axial extension, said inclination being less than 90°. Thereby these faces will ride each other when the first unit is turned in relation to the second unit about an axis defined by the axial extension of the female and the male part, whereby an axially extending force component is provided that releases the engagement between the sealing elements, ie a deactivation of the locking device simultaneously with the male part moving away from the female part when said faces ride each other. The faces may extend continuously around the male or the female part.

The connecting piece comprises two units—a first and a second unit—of which the one unit is constituted by a female part, while the second unit is constituted by a male part. During assembly of male and female part a close connection is provided due to the provision at the upper part of the male part of sealing elements and certain locking elements, on the one hand in the form of an annularly extending recess and, on the other, in the form of a flange. An annular recess fits into a corresponding annular bead mounted on the inner face of the female part, and where a click is provided, ie audible locking, when this recess engages around the bead. Moreover the female part comprises an annular recess, the side faces of which are axially parallel with the axis of the female part, and wherein they engage and enclose the flange of the male part. Firstly, good sealing is accomplished by this, since a sealing is provided both between recess and bead, which—as it is—also provide the locking device, and likewise a further safety sealing is accomplished between the flange and the annular recess. It is thus possible to avoid liquid seepage even when a liquid pressure of at least 125 mm bar is applied to the assembly.

At the opposite end of the female part, where the tubular part terminates, a delimiting edge is provided in the form of an edge that follows the shape of a wave, preferably with at least two tongues that are even and extend continuously in their circumference. The delimiting edge that follows the shape of a wave is congruent with a correspondingly configured collar that appears mounted around the outside of the male part and in the area that is at a distance, typically 1-2 cm, from the locking and sealing elements of the male part.

If a turning is subsequently performed of the male part, either in the one or the other direction, the inclining walls provided due to the waved shape on both the male and the female part will push against each other and hence push the assembly apart and break the locking connection established between the male part and the female part in the sealing area. Hereby easy separation of the two units is accomplished without considerable use of external forces, and likewise the sealing between the male and the female part is exceptionally good. The separator elements on the one hand and the sealing and locking elements on the other hand are constructed and operate independently of each other.

Provision of a connecting piece according to the invention provides a convenient configuration of the delimiting edge of the female part and the collar of the male part, such that the convenient separation may take place. Since the distance measured between the wave crests is the same all the way around, heeling of the male part when twisted is obviated since the separation forces will be evenly distributed on all sides of the male and the female part. Besides, the shape ensures that the transition between male and female part is smooth and thus tearings do not occur either.

By providing a connecting piece having the first sealing elements including an annularly extending bead arranged on the inner face of the female part and the second sealing elements including an annular recess arranged on the outer face of the male part to provide a lock, one the one hand good sealing is accomplished and, on the other, convenient locking between the male and the female part, and wherein this locking can be heard, as a clicking sound will be generated when the recess travels past the bead.

By providing a connecting piece including the first sealing elements having an annular recess, the delimiting side faces of which are essentially axially parallel with the centre axis of the female part and the second sealing elements have an annular flange for providing the delimiting edge of the male part, a further sealing is accomplished, which sealing as such comprises both the lateral and the medial side of the flange.

By providing a connecting piece having delimiting side faces of the annular flange of the male part extending taperingly in relation to the central axis of the flange and converging towards the delimiting edge of the flange and having a medially arranged side face for the annular recess of the first sealing elements including a beveling where the beveling faces laterally, it is accomplished that the flange slides into the annular recess and without a risk of being positioned erroneously during assembly.

By providing a connecting piece having one face of the annular band of the female part extending taperingly and converging in a direction towards the annular recess, it is accomplished that the recess will, with the least possible resistance slide across the bead, while simultaneously the height of the bead as such brings about good locking and good sealing.

By providing a connecting piece having the first connecting unit including a valve, regulation of the liquid connection through the connecting piece is accomplished, since it is the primary objective of the connecting piece to adjust the emptying of bags, eg urine bags.

By providing a connecting piece having a valve where the valve includes a housing having a displacer means which is displaceable within the housing and perpendicular to the central axis of the first connecting unit, and provided for regulating the passage of liquid in the first connecting unit, a convenient and simple manner of providing the valve's on/off function is accomplished.

By providing a connecting piece having displacer means including stops mounted at each end of the displacer means, it is accomplished that there is no risk of the displacer means sliding out of its housing when it is activated.

The invention further relates to use of the connecting piece and wherein this connecting piece, typically to the female portion as such, is associated with a catheter or a tubing for being connected to a urine bag, while the male part is connected to a tube or the tubing of a urine emptying bag, the idea behind the invention being that it is to be used for the emptying of leg or night urine bags to large collector receptacles. In that connection the male and female part will typically be disconnected, since, of course, the displacer means is closed such that no seepage of liquid occurs. When the leg bag is replete, a male part with connection to a collector receptacle is seized and inserted into the connecting piece and the displacer means is displaced to its position such that free liquid passage is allowed.

BRIEF DESCRIPTION OF THE SEVERAL VIEWS OF THE DRAWINGS

The invention will now be explained in further detail with reference to the drawing, wherein

FIGS. 1 and 2 show a connecting piece 1 comprising a first unit 3 and a second unit 4, wherein the first unit 3 constitutes the so-called female part. The first unit 3 comprises a first connecting part 5 configured as a stub and for being connected to a tubing 2 in the form of a tubing element 6 that is connected primarily to a urine bag or constitutes a catheter tubing. Opposite the tube stub the second connecting element 7 is arranged, which is also hollow and cylindrically tubular such that liquid is enabled to pass from the first connecting part 5 to the second connecting part 7.

DETAILED DESCRIPTION

Figure 1:
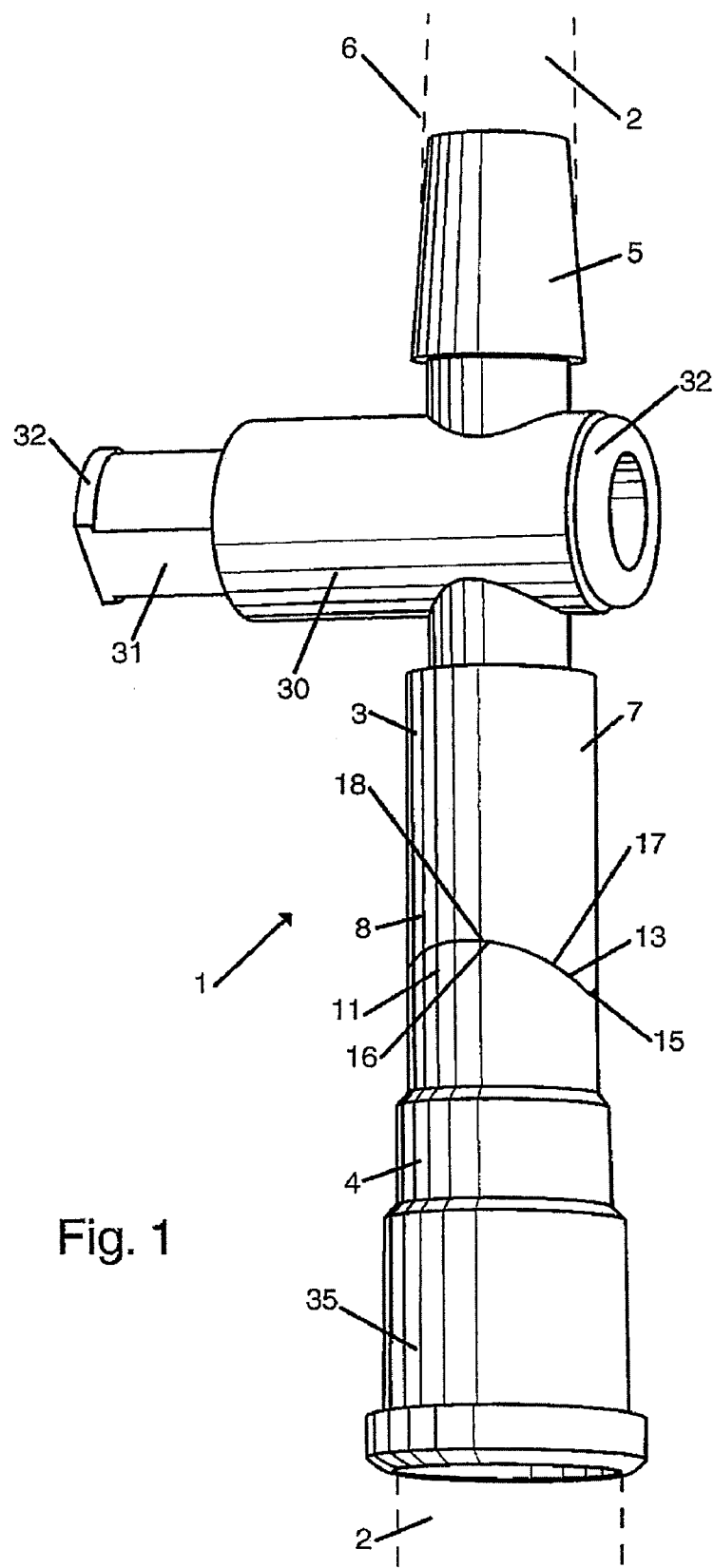
FIG. 1 is an exemplary embodiment of a connecting bag according to the invention and seen in a perspective view.
Figure 2:
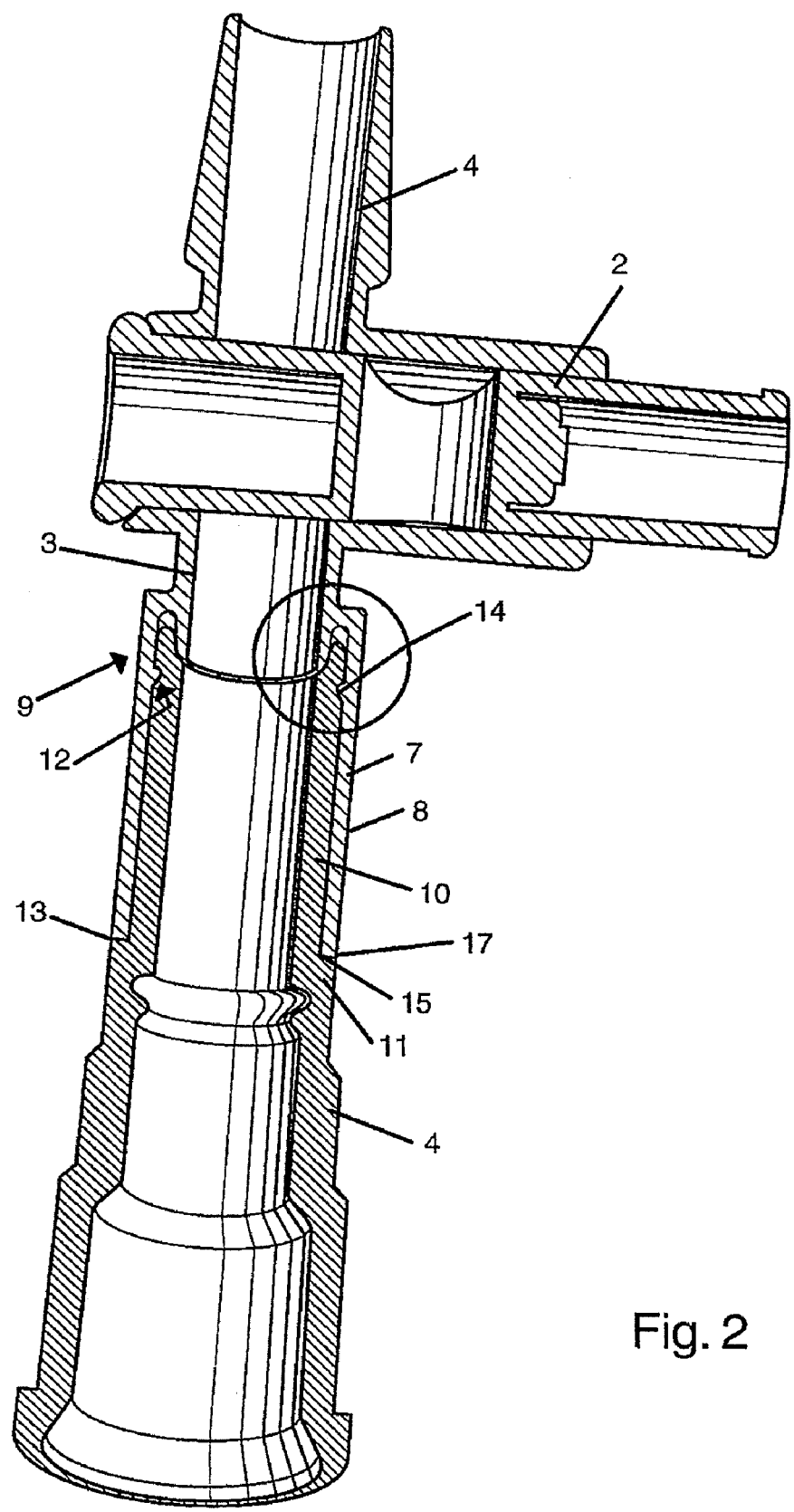
FIG. 2 shows the disclosures of FIG. 1, shown cut through in the central plane.
Figure 3:
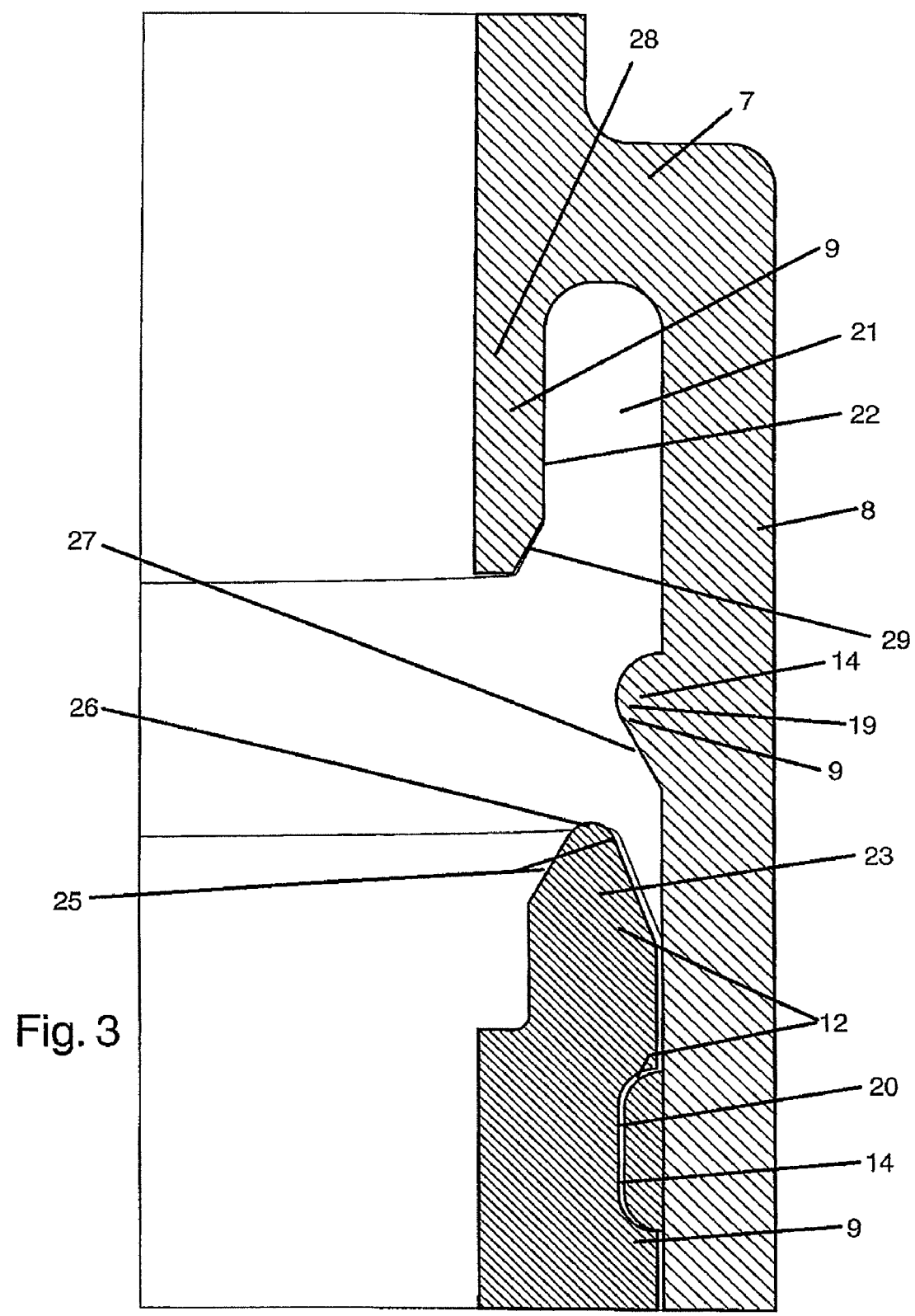
FIG. 3 is a sectional view of the section encircled in FIG. 2.

Typically, between the first and the second connecting part a valve 30 is introduced, said valve 30 being in its inner cavity provided with a displacer means 31 that has an opening and a closing position. In the opening position liquid may penetrate through a bore opening in the displacer means, the outer face of the displacer means being congruent with the inner faces of the valve housing, while, in its closing position, it will perform a closing of the liquid passage that exists between the first and the second connecting part.

Moreover, at each end the displacer means is provided with so-called stops 32, ie annularly extending beads having a larger diameter than the displacer means and the interior diameter of the housing as such, whereby it is prevented that the displaceable displacer means 31 is offset entirely out of the housing during use there of.

The second connecting part (7), which is thus a female part, encloses the second unit 4 of the connecting piece 1, which is, in principle, a male part, and comprising a tubular section of male part 10.

The second unit will, opposite the other end, be provided with a stub 35 into which a tubing can be shifted, whereby further liquid passage through the entire connecting piece 1 is enabled through this tubing 2. As mentioned, the second tubing comprises this male part, whose outer face is essentially congruent with the inner face of the female part and is delimited by a collar 11, said collar 11 having a delimiting 15 which follows the shape of a wave such that undercuts are not formed.

This means that the delimiting edge 15 of the collar is a continuously extending delimiting edge in such a manner that a connecting line between any two points in relation to the horizontal plane does not exceed 90°. Typically the collar will comprise two tongues 16, and wherein these tongues are arranged diametrically opposite each other.

The delimiting edge 17 of the female part will have a course that is congruent with the delimiting edge 15 of the collar and having an outer diameter that corresponds to the outer diameter of the collar to the effect that there is an even transition from the first unit 3 to the second unit 4. During twisting, ie dismounting of the second unit 4 from the first unit 3, they are turned in mutually opposite directions, whereby forces are transmitted in the edge area between the delimiting edges of the female and male parts, and due to the inclined course, a turning off will occur, whereby the rotating movement is translated into an axially extending force component, whereby the male part is shifted out of the enclosure of the female part.

However, the delimiting edge 15 of the collar may assume several shapes other than the waved shape; it may be eg triangular flaps/tongues, and likewise there may be more than two. It is essential, however, that there are no less than two, precisely to ensure that the male part is not twisted wrongly during dismounting.

Figure 7:
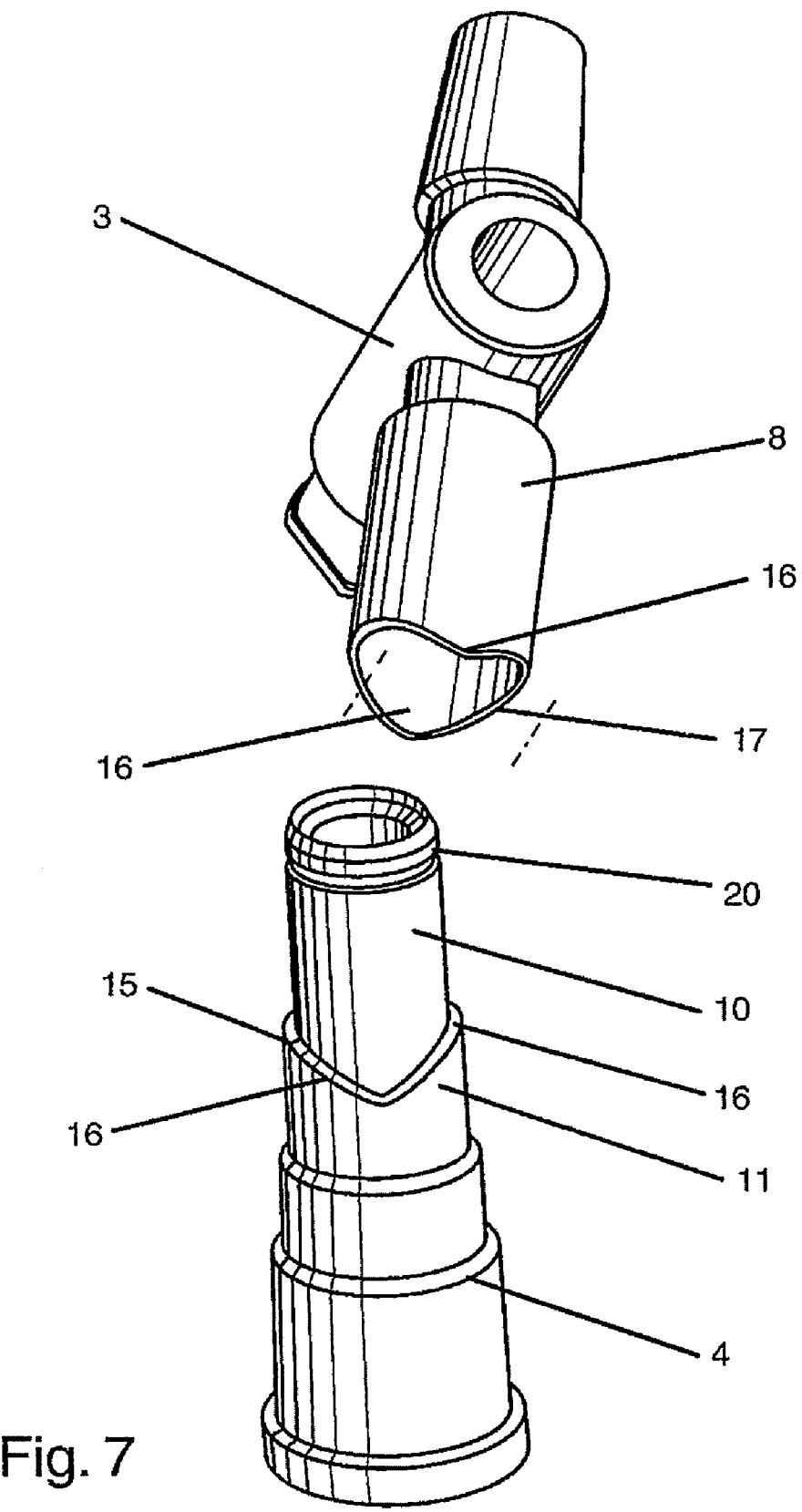
FIG. 7 shows the male and the female parts, separate and in perspective view.

FIG. 7 shows the waved course of the collar for providing two tongues and the corresponding congruent course of the female part for also providing two tongues.

The area between the delimiting edges of the male and the female part thus constitutes the separator elements 13 of the connecting piece 1. Opposite this area, inasmuch as the tubular part 8 of the male part is concerned, the sealing elements 9, 12 as such are arranged as is the locking device 14 that will be subject to further discussion with reference to FIGS. 3-6.

The locking device 14 comprises essentially that the upper delimiting edge of the male part comprises an annular recess 20 which is thus open in radial direction. This recess, which will typically be about ¼ mm deep, will, during locking, enclose a bead 19 that extends annularly on the inner faces of the female part, designated first sealing elements 9, whereas the annular recess on the male part are designated second sealing elements 12, these two constructions, in addition to ensuring a locking between the male and the female parts, also contributing to ensuring a liquid-proof assembly between the male and the female part.

The male part comprises a delimiting edge configured as an annularly extending flange 23, said annularly extending flange being delimited by taperingly extending delimiting side faces 25 that converge towards the delimiting edge 26 of the flange.

The bead also having a taperingly extending face 27, the inclination of which corresponds essentially to the laterally facing, inclined side face of the annularly extending flange, small resistance is ensured when the male part is displaced into the female part, also since the flange has a smaller thickness than the remainder of the tubing thickness of the male part and therefore the flange part is more flexible.

The sealing elements 9 comprise elements on the female part in the form of an annular recess 21 that forms a kind of pocket and wherein the delimiting side faces 22 of this annularly extending recess 21 are axially parallel to the centre axis of the female part. Essentially, this annularly extending recess has a width dimension that corresponds to the thickness of the flange. When the flange is shifted down into this annularly extending recess, it will typically be pressed against the side faces, preferably the side face located medially to the recess, whereby an additional sealing is accomplished. At the same time this arrangement of the flange, and as will also appear from FIG. 6, will ensure an improved and close abutment of the annular recess that is pressed against the annular bead 19. It should moreover be mentioned that the medially arranged side face 28 for the annular recess in the delimiting edge comprises a laterally oriented beveling 29, the angle of which corresponds essentially to the medially oriented, inclined face 25 of the flange, such that there is minimum resistance when the flange slides into the annular recess.

Figure 4:
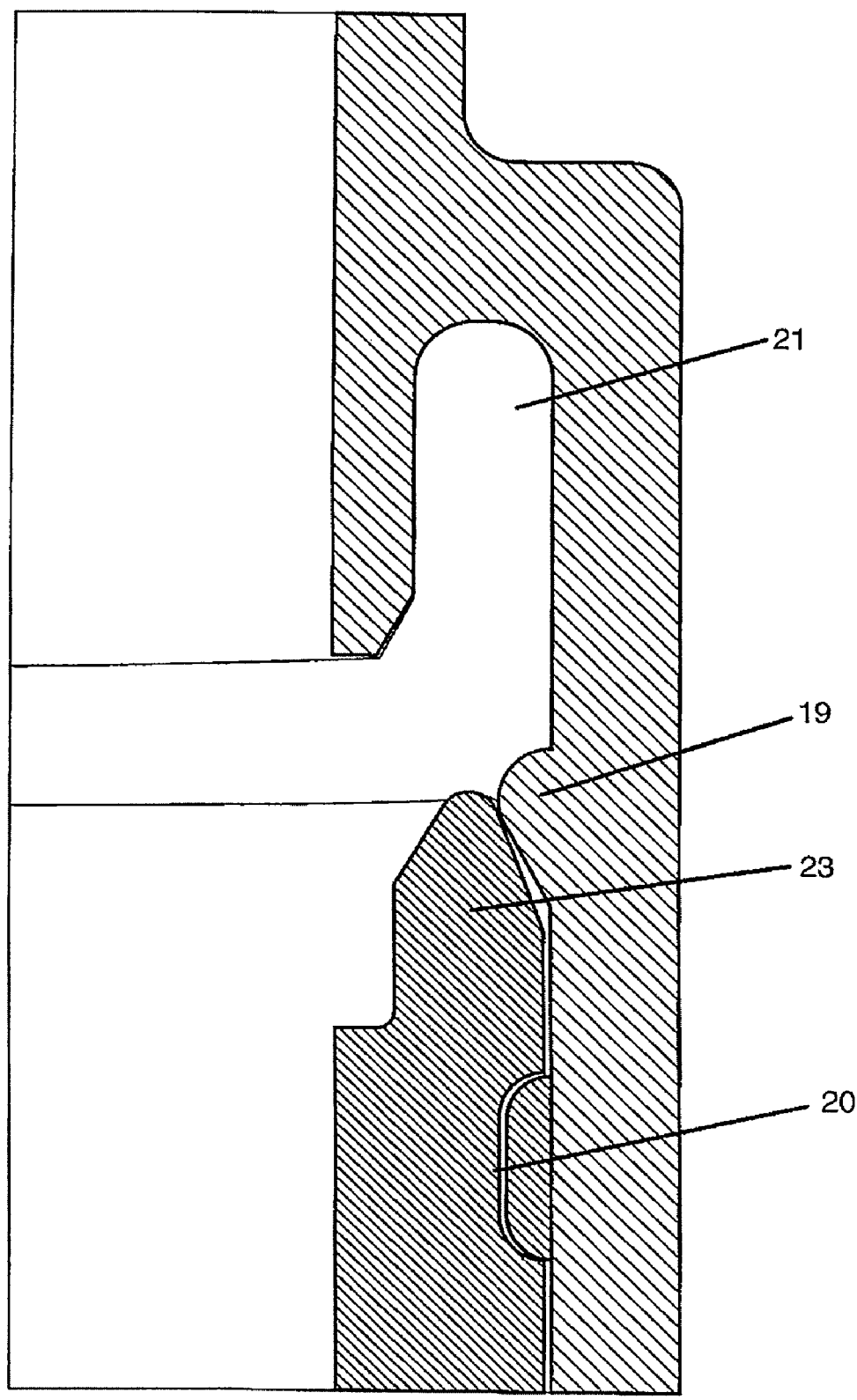
FIGS. 4, 5, 6 show different situations for the mutual arrangement of the male and the female parts during their assembly.
Figure 5:
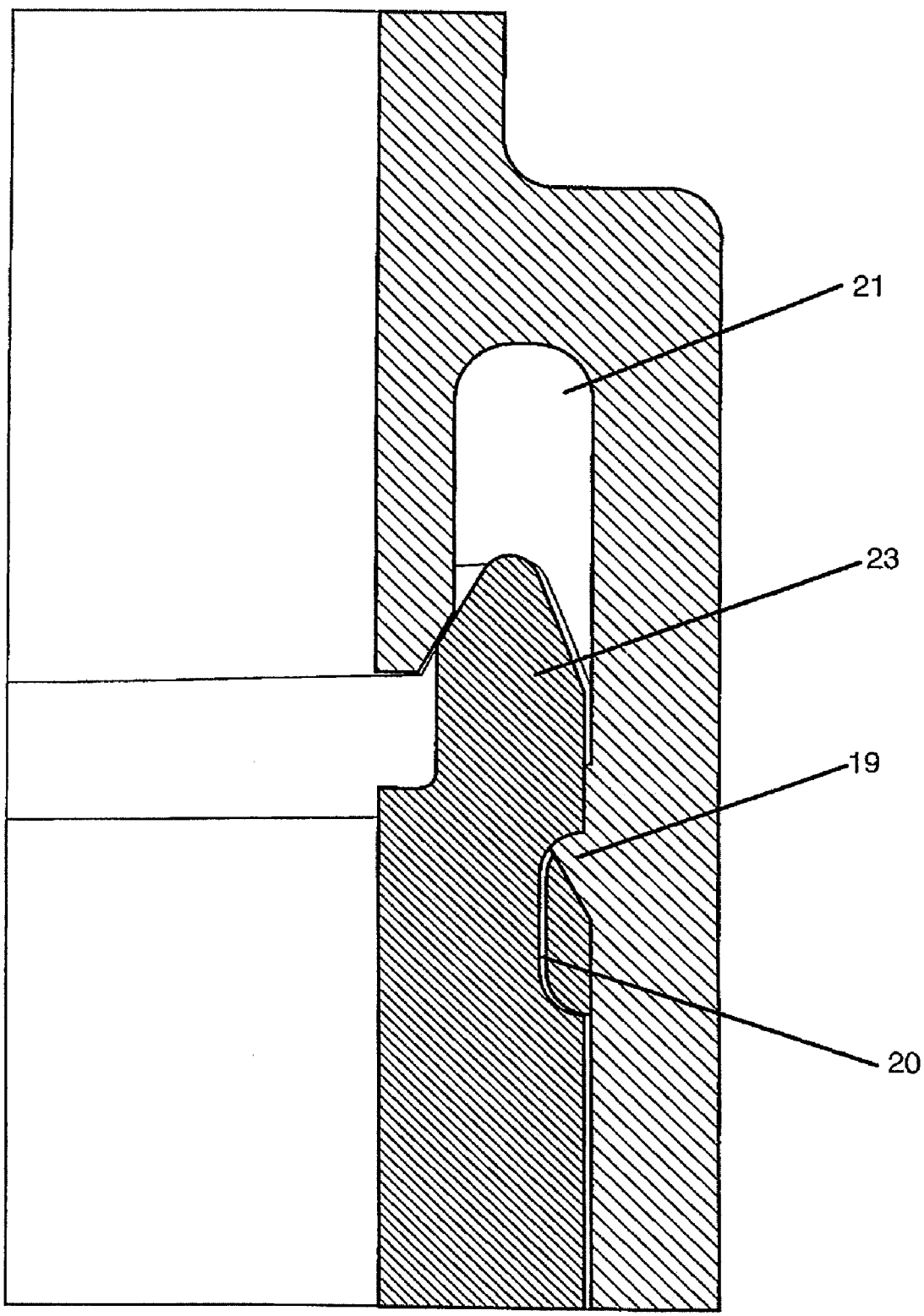

FIGS. 4-5 show different situations during assembly of the male and the female part.

Figure 6:
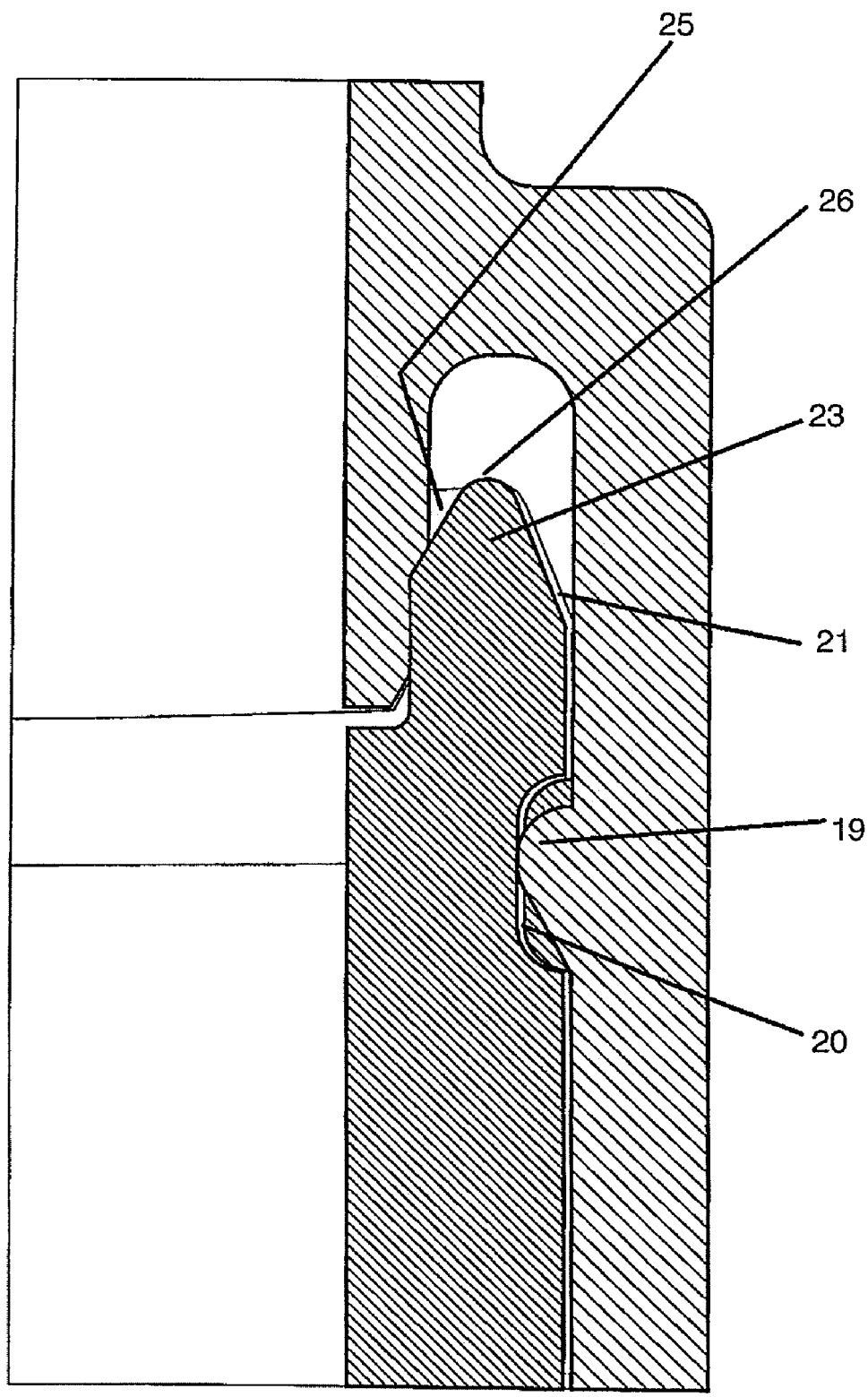

FIG. 6 shows when the male part is arranged in the female part and the locking device is activated, ie the annular bead 19 is enclosed by the annularly extending recess 20 on the outer face of the male part, and that the annularly extending flange 23 og the male part is situated in the annular recess of the female part, and wherein the medially facing delimiting face 25' of the flange 23 presses against the laterally facing side of the medially delimiting wall of the annular recess, whereby a sealing occurs in that area, simultaneously with a pressing occurring between bead 19 and the annular recess 20. Hereby forceful sealing is ensured, and likewise the delimiting edge 26 of the flange presses upwards into the bottom of the annular recess and thus ensures yet a sealing.

Figure 8:
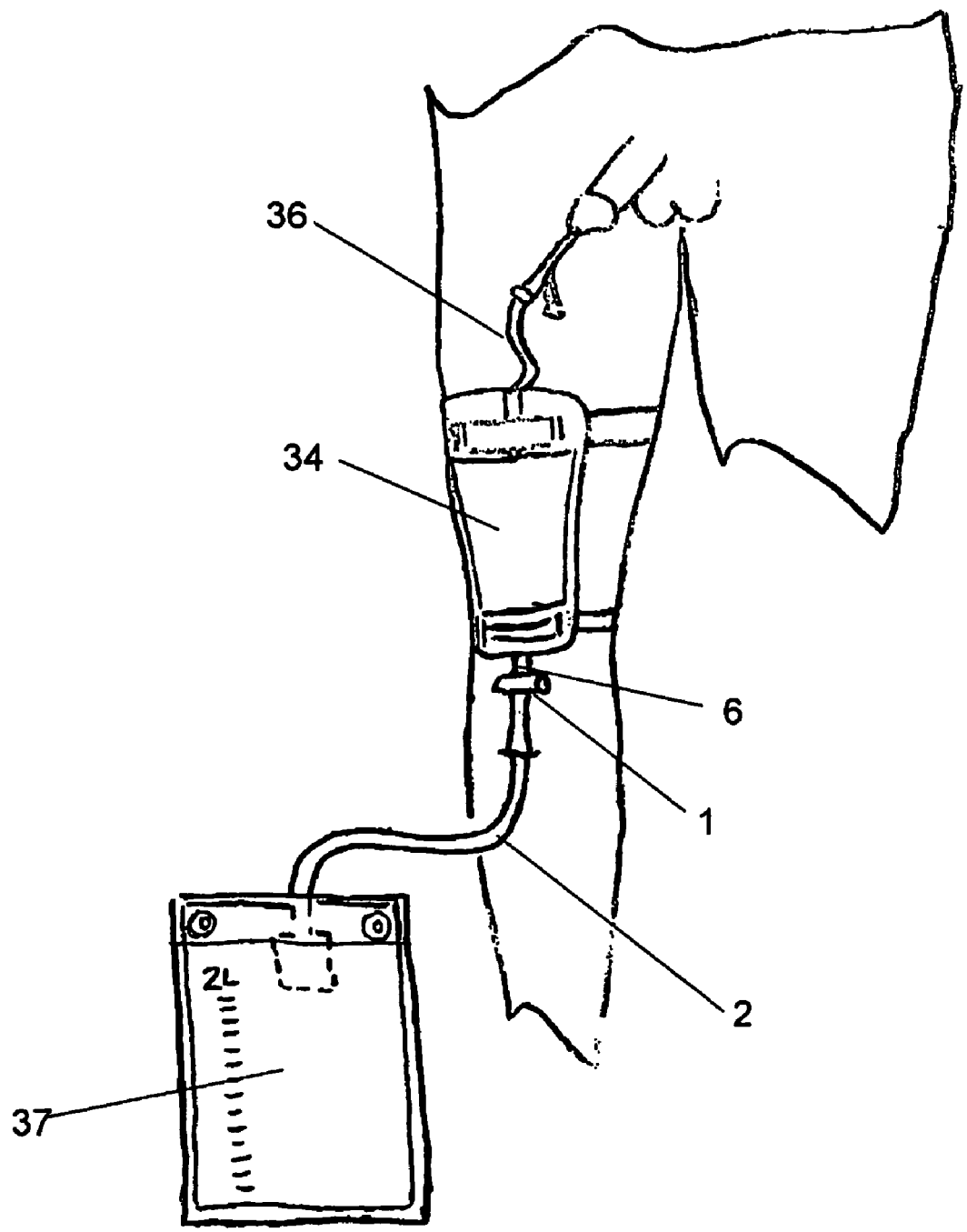
FIG. 8 shows the connecting piece for use in connection with a urine leg bag and a collector bag.

FIG. 8 shows the use of a connecting piece 1, wherein a leg bag 34 is connected to the leg of a patient, and in the upper part there extends a catheter 36 from this leg bag for collecting urine, said catheter being connected to the urethra of the patient. Opposite the area where the catheter 36 is connected, the urine bag 34 is provided with a tubing element 6. This tubing element is further connected to a connecting piece 1 according to the invention. The tubing element is mounted to the first connecting element of the first unit, which is configured as a stub.

On the stub 35 of the male part there is also mounted a tubing 2 that is connected to a discharge/collector receptacle 37. When the leg bag 34 of the patient is thus filled, the discharge bag 37 will typically be mounted with the tubing 2, on which the male part is secured upwardly, into the female part as such. The displacer means is subsequently displaced in the valve to the effect that the flow of liquid travels unimpeded through the connecting piece, following which the urine collected in the leg bag 34 is discharged into the collector bag 37. Subsequently the collecting receptacle 37 can be moved, as the displacer means is yet again arranged such that there is no passage of liquid within the connecting piece, and the male part in the connecting piece is dismounted from the female part following which the leg bag 34 is ready for renewed use.

The invention claimed is:

1. A connecting piece for a medical tubing, said connecting piece comprising a first unit and a second unit,
    said first unit comprising a first connecting element for a tubing element and a second connecting element for the second unit, said second connecting element comprising a tubular female part for engagement with the second unit and first sealing elements,
    said second unit comprising a tubular male part having a tubular portion fitting inside and surrounded by a portion of said tubular female part, and having a collar including a continuously extending delimiting edge defining a face on said male part, a connecting line between any two points along said delimiting edge in a peripheral direction of the male part being less than 90° in relation to an axial extension of said male part and said female part, said tubular portion of said male part having second sealing elements for cooperating with the first sealing elements,
    said first unit and second unit comprising respective separator elements, the first sealing elements and the second sealing elements configured for being mutually lockingly engageable by moving the male part and the female part axially towards each other, said mutual locking engagement establishing a lock, by which the first unit and the second unit are kept together with said tubular portion of said male part extending inside said female part;

the separator elements comprising a face arranged on the female part and a face arranged on the male part, said faces being in abutment against each other when the first unit and the second unit are kept together by said lock, said faces being such that by a turning of the first unit in relation to the second unit an axially extending positive force component is provided for by said face on said male part riding on said face on said female part, said positive force component forcing the first and second units to disengage and to leave their mutual engagement by axial displacement; and the separator elements being arranged in relation to said sealing elements such that said separator elements are at an axial distance from said lock when the first unit and the second unit are kept together by said lock.

2. A connecting piece according to claim 1, wherein the delimiting edge of the collar provides at least two tongues, and being congruent with a delimiting edge defining the face on the female part.

3. A connecting piece according to claim 1, wherein the delimiting edge of the collar follows the shape of a wave having a uniform distance between crests of the wave.

4. A connecting piece according to claim 1, wherein the first sealing elements comprise an annularly extending bead arranged on an inner face of the female part; and the second sealing elements comprise an annular recess arranged on an outer face of the male part, and which also provide the lock.

5. A connecting piece according to claim 1, wherein the first sealing elements comprise an annular recess including delimiting side faces being essentially axially parallel with a centre axis of the female part; and the second sealing elements comprise an annular flange for providing a second delimiting edge of the male part.

6. A connecting piece according to claim 5, wherein delimiting side faces of the annular flange of the male part extend taperingly in relation to a central axis of the annular flange and converge towards the second delimiting edge of the male part.

7. A connecting piece according to claim 6, wherein a face of an annular bead of the female part extends taperingly and converges in a direction towards the annular recess.

8. A connecting piece according to claim 5, wherein a medially arranged side face for the annular recess of the first sealing elements comprises a beveling, said beveling facing laterally.

9. A connecting piece according to claim 1, wherein the first connecting unit comprises a valve.

10. A connecting piece according to claim 9, wherein the valve comprises a housing having a displacer means which is displaceable within the housing and perpendicular to the central axis of the first connecting unit, being intended for regulating the passage of liquid in the first connecting unit.

11. A connecting piece according to claim 10, wherein the displacer means comprises stops mounted at each end of the displacer means.

12. A device for leak-proof connection of medical tubing, said device comprising a first unit and a second unit;
said first unit comprising:
a connecting portion that is connectable to a first medical tube,
a tubular female portion defining an axial direction of said device and having a through-going passage, said tubular female portion comprising first sealing elements arranged within said through-going passage, and
at least one first face disposed along a periphery of said first unit, said second unit comprising:
a connecting portion that is connectable to a second medical tube,
a tubular male portion comprising second sealing elements, said tubular male portion being receivable inside said through-going passage of said tubular female portion, and
at least one second face disposed along a periphery of said second unit,
said first and second sealing elements are lockable together to form a leak-proof engagement when said tubular male portion is received inside said through-going passage of said tubular female portion, said first and second sealing element engagement locking said tubular male portion against withdrawal from said tubular female portion,
said at least one first face is movable along said at least one second face from said engagement and said tubular male portion being twistable relative to said tubular female portion to provide a force in said axial direction for driving said first unit away from said second unit to disengage said first unit from said second unit,
said at least one first face is axially spaced apart from said first sealing elements and said at least one second face is axially spaced apart from said second sealing elements.

13. The device of claim 12, wherein said first face winds around a part of said first unit.

14. The device of claim 12, wherein said second face winds around a part of said second unit.

15. The device of claim 12, wherein an inner face of said female tubular portion has an annularly extending bead defining said first sealing elements and wherein an outer face of said male tubular portion has an annular recess defining said second sealing elements.

16. The device of claim 12, wherein an inner face of said female tubular portion has an annularly extending recess defining said first sealing elements and wherein said male tubular portion has an annular projection defining said second sealing elements.

17. A device for leak-proof connection of medical tubing, said device comprising a first unit releasably connected to a second unit;
said first unit comprising:
a connecting portion that is connectable to a first medical tube,
a tubular female portion defining an axial direction of said device and having a through-going passage, and
at least one first face disposed along a periphery of said first unit, said second unit comprising:
a connecting portion that is connectable to a second medical tube,
a tubular male portion, and
at least one second face disposed along a periphery of said second unit,
said tubular male portion being received inside said through-going passage of said tubular female portion,
said tubular female portion comprising first sealing elements arranged within said through-going passage, and
said tubular male portion comprising second sealing elements,
said first and second sealing elements being in leak-proof engagement with each other and releasably locking said tubular male portion against withdrawal from said tubular female portion, said at least one first face is movable along said at least one second face when said tubular female portion is twisted relative to said tubular male portion, to provide a force in said axial direction for driving said second unit away from said first unit to disengage said second unit from said first unit, said at least one first face is axially spaced apart from said first sealing elements and said at least one second face is axially spaced apart from said second sealing elements.

18. The device of claim 17, wherein said first face winds around a part of said first unit.

19. The device of claim 17, wherein said second face winds around a part of said second unit.

20. The device of claim 17, wherein an inner face of said female tubular portion has an annularly extending bead defining said first sealing elements and wherein an outer face of said male tubular portion has an annular recess defining said second sealing elements.

21. The device of claim 17, wherein an inner face of said female tubular portion has an annularly extending recess defining said first sealing elements and wherein said male tubular portion has an annular projection defining said second sealing elements.

\* \* \* \* \*